United States Patent
Jackson et al.

(10) Patent No.: US 11,559,882 B2
(45) Date of Patent: *Jan. 24, 2023

(54) TORQUE SENSOR

(71) Applicant: CMR SURGICAL LIMITED, Cambridge (GB)

(72) Inventors: Thomas Bates Jackson, Cambridge (GB); Edward John Mottram, Cambridge (GB); Gordon Thomas Deane, Cambridge (GB); Keith Marshall, Cambridge (GB); Paul Christopher Roberts, Cambridge (GB); Ricardo Michael Henderson Da Silva, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/153,155

(22) Filed: Jan. 20, 2021

(65) Prior Publication Data
US 2021/0138636 A1     May 13, 2021

Related U.S. Application Data

(63) Continuation of application No. 15/743,406, filed as application No. PCT/GB2016/052262 on Jul. 22, 2016, now Pat. No. 10,926,404.

(30) Foreign Application Priority Data

Jul. 22, 2015  (GB) .................................. 1512960
Jul. 22, 2015  (GB) .................................. 1512962
Jul. 22, 2015  (GB) .................................. 1512963

(51) Int. Cl.
*B25J 13/08*        (2006.01)
*G01L 3/10*        (2006.01)
(Continued)

(52) U.S. Cl.
CPC ............... *B25J 9/102* (2013.01); *A61B 34/30* (2016.02); *B25J 9/046* (2013.01); *B25J 9/126* (2013.01);
(Continued)

(58) Field of Classification Search
CPC ... B25J 9/102; B25J 9/046; B25J 9/126; B25J 17/0258; A61B 34/30; F16H 19/001;
(Continued)

(56) References Cited

U.S. PATENT DOCUMENTS 3,663,877 A     5/1972  Clark
4,435,120 A     3/1984  Ikeda et al.
(Continued)

FOREIGN PATENT DOCUMENTS

CN          2492352 Y      5/2002
CN        101325920 A     12/2008
(Continued)

OTHER PUBLICATIONS

Chinese First Office Action from corresponding Chinese Application No. 201680042744.7 dated Jul. 30, 2020.
(Continued)

*Primary Examiner* — Victor L MacArthur
*Assistant Examiner* — Gregory T Prather
(74) *Attorney, Agent, or Firm* — Lando & Anastasi, LLP

(57) ABSTRACT

Aspects of the disclosure include a torque sensor arrangement configured to attach between a first part and a second part to sense torque therebetween, the torque sensor arrangement comprising an interface member having on its exterior an engagement configuration configured to rotationally engage the first part, a torsion member comprising a deflectable body attached at one end thereof to the interface member and comprising, at the other end of the deflectable body, an engagement configuration configured to fixedly
(Continued)

engage the second part, and a deflection sensor attached to the deflectable body, wherein the interface member defines a rigid sleeve extending around the deflectable body and the torque sensor arrangement further comprises a bushing located between and in contact with both the sleeve and the deflectable body.

14 Claims, 11 Drawing Sheets

(51) Int. Cl.
    *B25J 9/10*           (2006.01)
    *G01L 5/22*           (2006.01)
    *B25J 17/02*          (2006.01)
    *A61B 34/30*         (2016.01)
    *B25J 9/04*           (2006.01)
    *B25J 9/12*           (2006.01)
    *G01D 5/244*         (2006.01)
    *F16H 19/00*         (2006.01)

(52) U.S. Cl.
    CPC ......... *B25J 13/085* (2013.01); *B25J 17/0258* (2013.01); *G01D 5/244* (2013.01); *G01L 3/108* (2013.01); *G01L 5/226* (2013.01); *A61B 2034/305* (2016.02); *F16H 19/001* (2013.01); *Y10S 901/09* (2013.01); *Y10S 901/15* (2013.01); *Y10S 901/23* (2013.01); *Y10S 901/26* (2013.01); *Y10S 901/29* (2013.01); *Y10S 901/46* (2013.01)

(58) Field of Classification Search
    CPC .. Y10S 901/001; Y10S 901/15; Y10S 901/23; Y10S 901/26; Y10S 901/29; Y10S 901/46; G01L 3/108
    See application file for complete search history.

(56) References Cited

U.S. PATENT DOCUMENTS

| | | |
|---|---|---|
| 4,760,753 A | 8/1988 | Vetter et al. |
| 4,761,114 A | 8/1988 | Barland |
| 4,776,232 A | 10/1988 | Beyer |
| 4,785,674 A * | 11/1988 | Orman ............... G01L 3/108 482/901 |
| 4,810,967 A | 3/1989 | Yokoyama et al. |
| 5,101,681 A | 4/1992 | Shpigel |
| 5,194,771 A | 3/1993 | Otsuki et al. |
| 5,581,166 A | 12/1996 | Eismann et al. |
| 5,703,623 A | 12/1997 | Hall et al. |
| 5,805,140 A | 9/1998 | Rosenberg et al. |
| 6,602,042 B2 | 8/2003 | Roy et al. |
| 6,699,177 B1 | 3/2004 | Wang et al. |
| 6,723,106 B1 | 4/2004 | Charles et al. |
| 6,871,563 B2 | 3/2005 | Choset et al. |
| 6,973,734 B2 | 12/2005 | Raab et al. |
| 8,380,351 B2 | 2/2013 | Okuda et al. |
| 8,413,538 B2 | 4/2013 | Haniya et al. |
| 8,414,043 B2 | 4/2013 | Albin et al. |
| 8,616,088 B2 | 12/2013 | Teng et al. |
| 8,621,955 B2 | 1/2014 | Long |
| 8,649,906 B2 | 2/2014 | Bischoff et al. |
| 8,663,060 B2 | 3/2014 | Cline |
| 8,997,599 B2 | 4/2015 | Maisonnier et al. |
| 9,010,214 B2 | 4/2015 | Markvicka et al. |
| 9,346,162 B2 | 5/2016 | Hashiguchi et al. |
| 9,724,168 B2 | 8/2017 | Yeung |
| 9,827,058 B1 | 11/2017 | Yeung et al. |
| 9,966,816 B2 | 5/2018 | Kokubo et al. |
| 10,161,816 B2 * | 12/2018 | Jackson ............... B25J 13/085 |
| 10,702,347 B2 | 7/2020 | Farritor et al. |
| 11,135,023 B2 | 10/2021 | Larkin et al. |
| 2003/0218458 A1 | 11/2003 | Seger et al. |
| 2004/0070391 A1 | 4/2004 | Muszynski |
| 2004/0136628 A1 | 7/2004 | Inoue |
| 2004/0178757 A1 | 9/2004 | Petersen |
| 2004/0250644 A1 | 12/2004 | Gosselin et al. |
| 2005/0103123 A1 * | 5/2005 | Newman ............... G01L 1/2218 73/862.045 |
| 2005/0275367 A1 | 12/2005 | Buehler et al. |
| 2006/0059698 A1 | 3/2006 | Staudt et al. |
| 2007/0151391 A1 * | 7/2007 | Larkin ............... A61B 34/76 74/490.06 |
| 2010/0090633 A1 | 4/2010 | Deller et al. |
| 2012/0045308 A1 | 2/2012 | Kremerman |
| 2012/0048628 A1 | 3/2012 | Kawanami et al. |
| 2012/0105055 A1 | 5/2012 | Takahashi et al. |
| 2012/0137816 A1 | 6/2012 | Carricato et al. |
| 2012/0143353 A1 | 6/2012 | Kishi |
| 2013/0013695 A1 | 1/2013 | Jin et al. |
| 2013/0131695 A1 | 5/2013 | Scarfogliero et al. |
| 2013/0340560 A1 | 12/2013 | Burridge et al. |
| 2013/0345717 A1 | 12/2013 | Markvicka et al. |
| 2014/0001231 A1 | 1/2014 | Shelton, IV et al. |
| 2014/0005662 A1 | 1/2014 | Shelton, IV |
| 2014/0005687 A1 | 1/2014 | Prisco et al. |
| 2014/0060223 A1 | 3/2014 | Tanaka |
| 2015/0068350 A1 | 3/2015 | Kirihara et al. |
| 2015/0265355 A1 | 9/2015 | Prestel et al. |
| 2016/0008989 A1 | 1/2016 | Bakir et al. |
| 2016/0101518 A1 | 4/2016 | Saito et al. |
| 2016/0114479 A1 | 4/2016 | Rosheim |
| 2016/0135898 A1 | 5/2016 | Frederick et al. |
| 2016/0175062 A1 | 6/2016 | Limon |
| 2016/0207206 A1 | 7/2016 | Sato et al. |
| 2016/0263749 A1 * | 9/2016 | Ogata ............... B25J 13/085 |
| 2016/0270780 A1 | 9/2016 | Hall et al. |
| 2016/0303745 A1 | 10/2016 | Rockrohr |
| 2016/0331482 A1 | 11/2016 | Hares |
| 2017/0014197 A1 | 1/2017 | McCrea et al. |
| 2017/0025974 A1 * | 1/2017 | Phan ............... H02K 15/02 |
| 2017/0049519 A1 | 2/2017 | Grover et al. |
| 2017/0205296 A1 | 7/2017 | Bradford |
| 2017/0211999 A1 | 7/2017 | Bradford et al. |
| 2017/0241813 A1 | 8/2017 | Ersek et al. |
| 2017/0265951 A1 | 9/2017 | Grover et al. |
| 2017/0302207 A1 | 10/2017 | Goossens et al. |
| 2017/0304015 A1 | 10/2017 | Tavallaei et al. |
| 2018/0116741 A1 | 5/2018 | Garcia Kilroy et al. |
| 2018/0209819 A1 | 7/2018 | Marshall et al. |
| 2018/0283842 A1 | 10/2018 | Rueb et al. |
| 2019/0101413 A1 | 4/2019 | Murata |

FOREIGN PATENT DOCUMENTS

| | | |
|---|---|---|
| CN | 201552579 U | 8/2010 |
| CN | 102284959 A | 12/2011 |
| CN | 102401709 A | 4/2012 |
| CN | 102431033 A | 5/2012 |
| CN | 102626930 A | 8/2012 |
| CN | 103561919 A | 2/2014 |
| CN | 104742152 A | 7/2015 |
| DE | 3528364 A1 * | 2/1987 |
| DE | 3528364 A1 | 2/1987 |
| DE | 10145234 A1 | 4/2003 |
| DE | 20220273 U1 | 9/2003 |
| DE | 102011108265 A1 | 1/2013 |
| EP | 0128544 A1 | 12/1984 |
| EP | 0279591 A1 | 8/1988 |
| EP | 2700481 A1 | 2/2014 |
| FR | 2504051 A1 | 10/1982 |
| FR | 2608756 A1 | 6/1988 |
| FR | 2832345 A1 | 5/2003 |
| GB | 1565730 A | 4/1980 |
| JP | S59073297 A | 4/1984 |
| JP | S6090693 A | 5/1985 |
| JP | S60167796 A | 8/1985 |
| JP | S61117696 U | 7/1986 |
| JP | S63047085 A | 2/1988 |
| JP | H06190770 A | 7/1994 |
| JP | 3013373 U | 7/1995 |

(56) References Cited

FOREIGN PATENT DOCUMENTS

| | | |
|---|---|---|
| JP | 2002530209 A | 9/2002 |
| JP | 2007502984 A | 2/2007 |
| JP | 2009297809 A | 12/2009 |
| JP | 2011516286 A | 5/2011 |
| JP | 2012-131014 A | 7/2012 |
| JP | 2014-237206 A | 12/2014 |
| JP | 2015072262 A | 4/2015 |
| SU | 1151453 A1 | 4/1985 |
| WO | 0030557 A1 | 6/2000 |
| WO | 2009124904 A1 | 10/2009 |
| WO | 2015088655 A1 | 6/2015 |
| WO | 2015132549 A1 | 9/2015 |

OTHER PUBLICATIONS

Chinese First Office Action from corresponding Chinese Application No. 201910252684.7 dated Nov. 18, 2021.
English Translation of Japanese Notification of Reasons for Refusal from corresponding Japanese Patent Application No. 2018-502792 dated Jul. 1, 2020.
Indian Examination Report from corresponding Indian Application No. 201817005622 dated Feb. 11, 2020.
Notification of Transmittal of the International Search Report and the Written Opinion of the International Searching Authority from corresponding PCT/GB2016/052262 dated Dec. 5, 2016.
United Kingdom Examination Report under Section 18 (3) from corresponding United Kingdom Patent Application No. GB1512960.4 dated Jul. 9, 2020.
United Kingdom Search Report from corresponding United Kingdom Application No. GB1512960.4 dated Dec. 24, 2015.
United Kingdom Search Report from corresponding United Kingdom Application No. GB1512962.0 dated Dec. 28, 2015.
United Kingdom Search Report from corresponding United Kingdom Application No. GB1512963.8 dated Feb. 29, 2016.
Japanese Decision to Grant a Patent from corresponding Japanese Patent Application No. 2021 119577 dated Aug. 25, 2022.

* cited by examiner

TORQUE SENSOR

CROSS-REFERENCE TO RELATED APPLICATIONS

This application is a continuation of U.S. patent application Ser. No. 15/743,406, which has a 371(c) date of Jan. 10, 2018 and which is a U.S. National Phase Application under 35 U.S.C. § 371 of International Application No. PCT/GB2016/052262, filed Jul. 22, 2016. International Application No. PCT/GB2016/052262 claims priority to United Kingdom Application No. GB1512960.4, filed Jul. 22, 2015, United Kingdom Application No. GB1512962.0, filed Jul. 22, 2015, and United Kingdom Application No. GB1512963.8, filed Jul. 22, 2015. Each application referenced above is hereby incorporated herein by reference in its entirety for all purposes.

BACKGROUND

This invention relates to drive arrangements for robot joints, with particular relevance to robot wrists.

Robots that are required to manipulate objects, which may for example be industrial or surgical robots, frequently have an arm composed of rigid elements which are linked together in series by a number of flexible joints. The joints could be of any type but are typically revolute joints, or a combination of revolute and prismatic joints. The arm extends from a base, whose location might be fixed or moveable, and terminates in a tool or an attachment for a tool. The tool could, for example be a gripping, cutting, illuminating, irradiating or imaging tool. The final joint in the arm may be termed the wrist. The wrist may permit motion about only a single axis, or it may be a complex or compound articulation, which permits rotation about multiple axes. As disclosed in our co-pending patent application PCT/GB2014/053523, the wrist may provide two roll joints whose axes are generally longitudinal to the arm, separated by two pitch/yaw joints, whose axes are generally transverse to the arm.

In the case of a surgical robot there are a number of important criteria that influence the design of the distal joint(s) of the arm.

1. It is desirable for the arm, and particularly its distal portion where the wrist is located, to be small in size. That allows multiple such robot arms to work in close proximity and hence opens up a wider range of surgical procedures that the arm can perform.
2. It is desirable for the outer profile of the distal portion of the arm to be circularly symmetrical about the length of the arm. This allows the distal portion to be rotated longitudinally without having to be repositioned if it is close to another robot, to some other equipment or to the patient.
3. It is desirably for the joints to be capable of delivering a high torque, so that they can carry heavier tools and deliver high acceleration to the tool tip.
4. It is desirable for the joints to be stiff, with little or no backlash or elasticity, so that when a tool tip has been positioned it will be fixed in position. A conventional approach to minimizing backlash is to designate one or more gear elements as sacrificial, but this requires a high level of maintenance, and can result in worn gear particles being liberated within the arm.
5. It is desirable for all articulations to have position and force/torque sensors, so that the control mechanism can take data from those sensors.
6. It is desirable for the distal portion of the robot arm to be as light as possible, to reduce the force that must be exerted by more proximal joints of the robot arm.
7. A typical robot arm carries cables that provide power to its drive motors and perhaps to a tool, and carry signals back from sensors such as position, torque and imaging sensors. It is desirable for the arm to include a path for such cables to pass in the interior of the arm.

The number of important criteria makes it difficult to design an arm that best balances all the requirements.

One particular problem is how to fit the motors and gearing into the wrist of a robot arm. The arrangement should be compact but also allow for high stiffness and torque transfer. Many existing designs compromise one of these criteria.

There is a need for an improved drive arrangement for a joint of a robot arm.

Another particular problem is how to fit the torque sensors into the wrist of a robot arm. The arrangement should be compact but also allow for high accuracy in torque measurement.

There is a need for an improved torque sensor arrangement for a joint of a robot arm.

Another particular problem is how to fit position sensors motors into the wrist of a robot arm. The arrangement should be compact but also allow for a high degree of accuracy.

There is a need for an improved position sensor arrangement for a joint of a robot arm and for other applications.

SUMMARY OF THE INVENTION

According to the present invention there is provided a robot arm comprising a joint mechanism for articulating one limb of the arm relative to another limb of the arm about two non-parallel rotation axes, the mechanism comprising: an intermediate carrier attached to a first one of the limbs by a first revolute joint having a first rotation axis and to a second one of the limbs by a second revolute joint having a second rotation axis; a first drive gear disposed about the first rotation axis and fast with the carrier, whereby rotation of the carrier relative to the first limb about the first rotation axis can be driven; a second drive gear disposed about the second rotation axis and fast with the second one of the limbs, whereby rotation of the second one of the limbs about the second rotation axis relative to the carrier can be driven; at least one of the first and second drive gears being a sector gear.

The first one of the first and second drive gears may be a sector gear. It may be that only one of the first and second drive gears is a sector gear. That may be the first or the second drive gear.

The or each sector gear may be a toothed gear.

The or each sector gear may be a bevel gear: i.e. a gear whose pitch surface is a straight-sided or curved cone and/or whose teeth are arranged on such a cone.

The operative sector of the or each sector gear may be less than 180°.

At least part of one of the drive gears may intersect a circle about the axis of the other one of the drive gears that is coincident with the radially outermost part of said other one of the drive gears.

The carrier may carry an intermediate linkage for conveying drive to one of the drive gears, and at least part of that linkage intersects a circle about the axis of the other one of the drive gears that is coincident with the radially outermost part of said other one of the drive gears.

One or both of the first drive gears may be bevel gear(s).

One or both of the first drive gears may be skew axis gear(s).

The first and second axes may be orthogonal. The first and second axes may intersect each other.

The or each sector gear may have a smaller outer radius in its non-operative sector than in its operative sector.

The arm may comprise: a third limb adjacent the first limb and on the opposite side of the first limb to the coupler; a fourth limb adjacent the second limb and on the opposite side of the second limb to the coupler; a third revolute joint whereby the third limb and the first limb are attached together, the third revolute joint having a third rotation axis orthogonal to the first rotation axis; and a fourth revolute joint whereby the fourth limb and the second limb are attached together, the fourth revolute joint having a fourth rotation axis orthogonal to the second rotation axis.

The first and third axes may be orthogonal for all configurations of the joints.

The second and fourth axes may be orthogonal for all configurations of the joints.

The more distal one of the third and fourth limbs may comprise a tool or a tool attachment.

One of the third and fourth limbs may be the most distal limb of the arm.

The third and fourth axes may be coincident for at least one configuration of the joints.

According to another aspect of the present invention there is provided a torque sensor arrangement for attachment between a first part and a second part to sense torque therebetween, the torque sensor arrangement comprising: an interface member having on its exterior an engagement configuration for rotationally engaging the first part; a torsion member comprising a deflectable body attached at one end thereof to the interface member and comprising, at the other end of the deflectable body, an engagement configuration for rotationally engaging the second part; and a deflection sensor attached to the deflectable body; wherein the interface member defines a rigid sleeve extending around the deflectable body and the torque sensor arrangement further comprises a bushing located between and in contact with both the sleeve and the deflectable body.

The bushing may be a solid bushing. The bushing may be a unitary tube of material. The bushing may be formed of plastics material.

The first part and the second part may be configured for mutual rotation about a rotation axis. The bushing may surround the deflectable body about that axis.

The bushing may be a rigid bushing.

The first part and the second part may be configured for mutual rotation about a rotation axis and the material of the bushing may be such as to substantially transfer shear load about that axis from the deflectable body to the sleeve and such as to substantially isolate torsion of the deflectable body from the sleeve.

The interface member may comprise a shoulder on the opposite side of the sleeve from that at which the torsion member is attached to the interface member. The torsion member may be configured to hold the bushing captive against the shoulder when the torsion member is attached to the interface member.

The deflectable body is a hollow body. The deflectable body may be a hollow cylinder. The deflectable body may be deflectable in torsion and/or bending about the axis of the cylinder.

The deflection sensor may be a strain gauge.

The engagement configuration for rotationally engaging the first part may be a set of gear teeth. The gear teeth may be of a bevel gear: i.e. a gear whose pitch surface is a straight-sided or curved cone and/or whose teeth are arranged on such a cone.

The engagement configuration for rotationally engaging the second part may be a spline coupling.

The interface member may be rotationally engaged with the first part. The torsion member may be rotationally engaged with the second part.

The torque sensor may be arranged for sensing torque between two limbs of a robot arm.

According to another aspect of the present invention there is provided a rotary position sensor arrangement for sensing rotary motion about a first rotation axis between a first part and a second part, the arrangement comprising: a first ring defining a plurality of magnetic poles, the first ring being attached to the first part; a second ring defining a plurality of magnetic poles, the second ring being attached to the first part; a first sensor attached to the second part for sensing motion of the magnetic poles of the first ring past that sensor; and a second sensor attached to the second part for sensing motion of the magnetic poles of the second ring past that sensor; the first ring and the second ring being spaced apart along the rotation axis.

The first part may comprises material interposed between the poles of the first and second rings. The said material may be metallic material. The said material may be non-magnetically susceptible material.

The first and second part may be attached by a pair of bearings defining a revolute joint about the rotation axis. The bearings may be located at the extremities of the interface between the first and second parts along the rotation axis. The first ring may be located at one of the bearings and the other ring may be located at the other of the bearings.

The first ring may be located so as to lie in a common plane perpendicular to the rotation axis with the said one of the bearings. The second ring may be located so as to lie in a common plane perpendicular to the rotation axis with the said other of the bearings.

The first ring may be located around the said one of the bearings. The second ring may be located around the said other of the bearings.

The spacing along the rotation axis between the first and second rings may be greater than 5 times the thickness of the rings in the direction along the rotation axis. If the rings are of different thicknesses, the spacing may be greater than 5 times the thickness of the thinner of the rings.

The second part may be a first limb of a robot arm. The first part may be a coupler whereby the first limb is attached to a second limb of the robot arm. The coupler may be a rigid element.

The coupler may be attached to the second limb by a revolute joint having a second rotation axis oblique, or more particularly orthogonal, to the first rotation axis.

The first and second sensors may be capable of sensing the relative position of poles of the rings thereto to a resolution of two bits or more than two bits. The rings may have different numbers of poles. The numbers may be co-prime.

BRIEF DESCRIPTION OF THE FIGURES

The present invention will now be described by way of example with reference to the accompanying drawings. In the drawings.

DETAILED DESCRIPTION

The wrist mechanisms to be described below have been found to provide compact and mechanically advantageous arrangements for at least some of the joints of a robot wrist, or for other applications.

Figure 1:
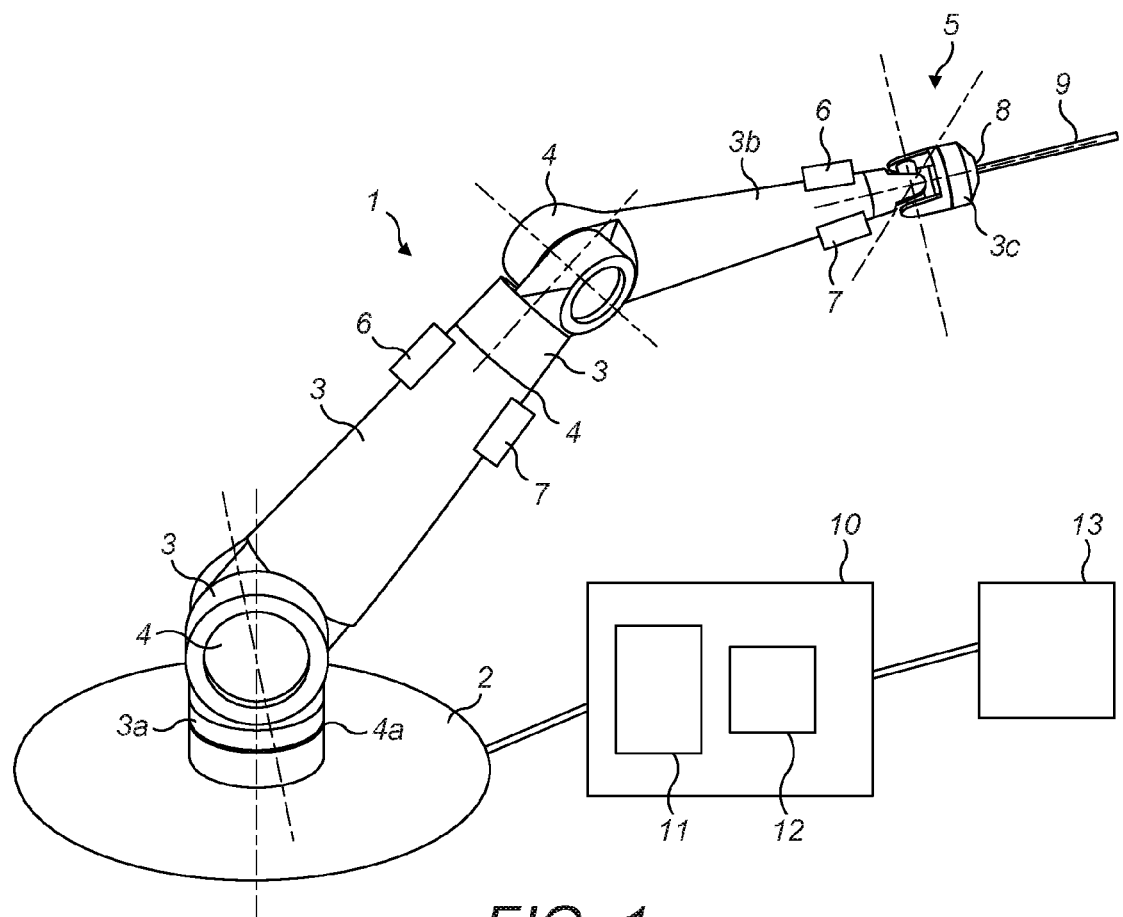
FIG. 1 is a general representation of a surgical robot arm.

FIG. 1 shows a surgical robot having an arm 1 which extends from a base 2. The arm comprises a number of rigid limbs 3. The limbs are coupled by revolute joints 4. The most proximal limb 3a is coupled to the base by joint 4a. It and the other limbs are coupled in series by further ones of the joints 4. A wrist 5 is made up of four individual revolute joints. The wrist 5 couples one limb (3b) to the most distal limb (3c) of the arm. The most distal limb 3c carries an attachment 8 for a surgical instrument or tool 9. Each joint 4 of the arm has one or more motors 6 which can be operated to cause rotational motion at the respective joint, and one or more position and/or torque sensors 7 which provide information regarding the current configuration and/or load at that joint. For clarity, only some of the motors and sensors are shown in FIG. 1. The arm may be generally as described in our co-pending patent application PCT/GB2014/053523. The attachment point 8 for a tool can suitably comprise any one or more of: (i) a formation permitting a tool to be mechanically attached to the arm, (ii) an interface for communicating electrical and/or optical power and/or data to and/or from the tool, and (iii) a mechanical drive for driving motion of a part of a tool. In general it is preferred that the motors are arranged proximally of the joints whose motion they drive, so as to improve weight distribution. As discussed below, controllers for the motors, torque sensors and encoders are distributed with the arm. The controllers are connected via a communication bus to control unit 10.

A control unit 10 comprises a processor 11 and a memory 12. Memory 12 stores in a non-transient way software that is executable by the processor to control the operation of the motors 6 to cause the arm 1 to operate in the manner described herein. In particular, the software can control the processor 11 to cause the motors (for example via distributed controllers) to drive in dependence on inputs from the sensors 7 and from a surgeon command interface 13. The control unit 10 is coupled to the motors 6 for driving them in accordance with outputs generated by execution of the software. The control unit 10 is coupled to the sensors 7 for receiving sensed input from the sensors, and to the command interface 13 for receiving input from it. The respective couplings may, for example, each be electrical or optical cables, or may be provided by a wireless connection. The command interface 13 comprises one or more input devices whereby a user can request motion of the arm in a desired way. The input devices could, for example, be manually operable mechanical input devices such as control handles or joysticks, or contactless input devices such as optical gesture sensors. The software stored in memory 12 is configured to respond to those inputs and cause the joints of the arm to move accordingly, in compliance with a pre-determined control strategy. The control strategy may include safety features which moderate the motion of the arm in response to command inputs. Thus, in summary, a surgeon at the command interface 13 can control the robot arm 1 to move in such a way as to perform a desired surgical procedure. The control unit 10 and/or the command interface 13 may be remote from the arm 1.

Figure 2:
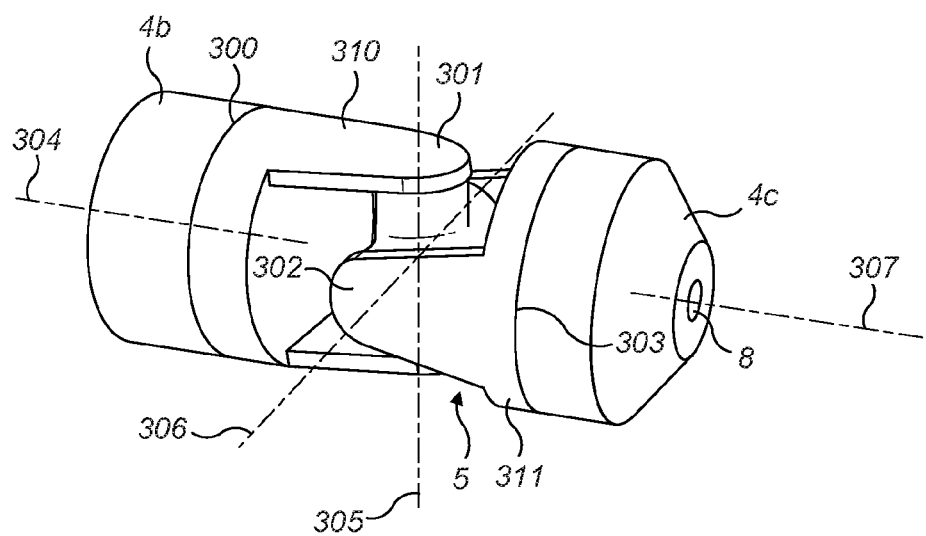
FIG. 2 shows in more detail the rotation axes at the wrist of the arm of FIG. 1.

FIG. 2 shows the wrist 5 of the robot in more detail. The wrist comprises four revolute joints 300, 301, 302, 303. The joints are arranged in series, with a rigid part of the arm extending from each joint to the next. The most proximal joint 300 of the wrist joins arm part 4b to arm part 310. Joint 300 has a "roll" rotation axis 304, which is directed generally along the extent of the limb 4b of the arm that is immediately proximal of the articulations of the wrist. The next most distal joint 301 of the wrist joins arm part 310 to arm part 311. Joint 301 has a "pitch" rotation axis 305 which is perpendicular to axis 304 in all configurations of joints 300 and 301. The next most distal joint 302 of the wrist joins arm part 310 to arm part 311. Joint 302 has a "yaw" rotation axis 306 which is perpendicular to axis 305 in all configurations of joints 301 and 302. In some configurations of the wrist, axis 306 is also perpendicular to axis 304. The next most distal joint of the wrist 303 joins arm part 311 to arm part 4c. Joint 303 has a "roll" rotation axis 307 which is perpendicular to axis 306 in all configurations of joints 302 and 303. In some configurations of the wrist, axis 307 is also perpendicular to axis 305 and parallel with (and preferably collinear with) axis 304. It is preferable for axes 305 and 306 to intersect each other, since this gives a particularly compact configuration. Joints 300 and 303 may be positioned so that axes 304 and 307 can pass through the intersection of axes 305, 306 for some configurations of the wrist.

This design of wrist is advantageous in that it allows a wide range of movement from a tool attached to the attachment point 8 at the distal end of arm part 4c, but with the wrist being capable of being assembled in a relatively compact form and without there being singularities at certain parts of the range of motion that could demand excessively high rates of motion at individual joints.

Figure 3:
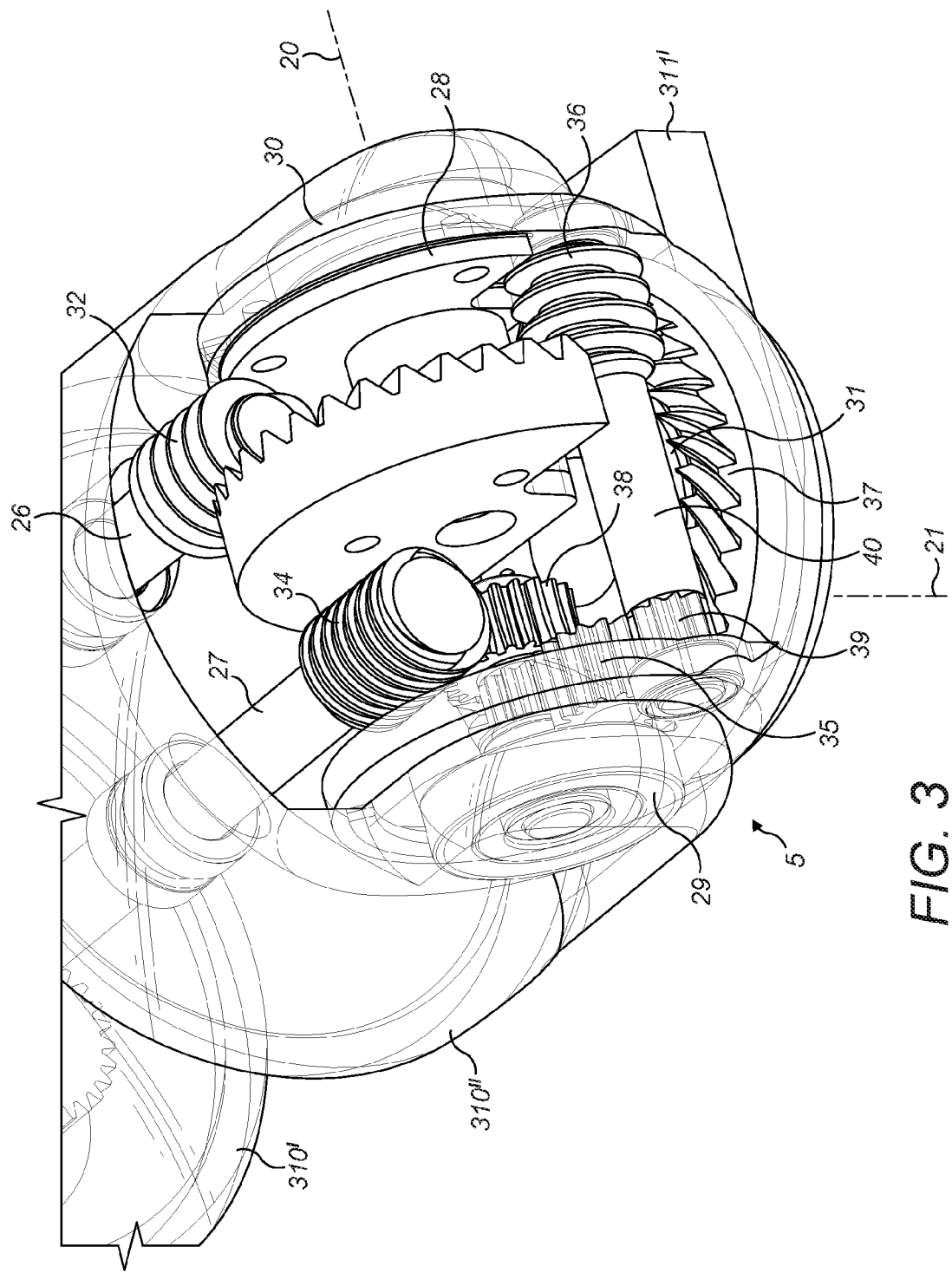
FIG. 3 shows part of a first wrist mechanism from distally and one side.
Figure 4:
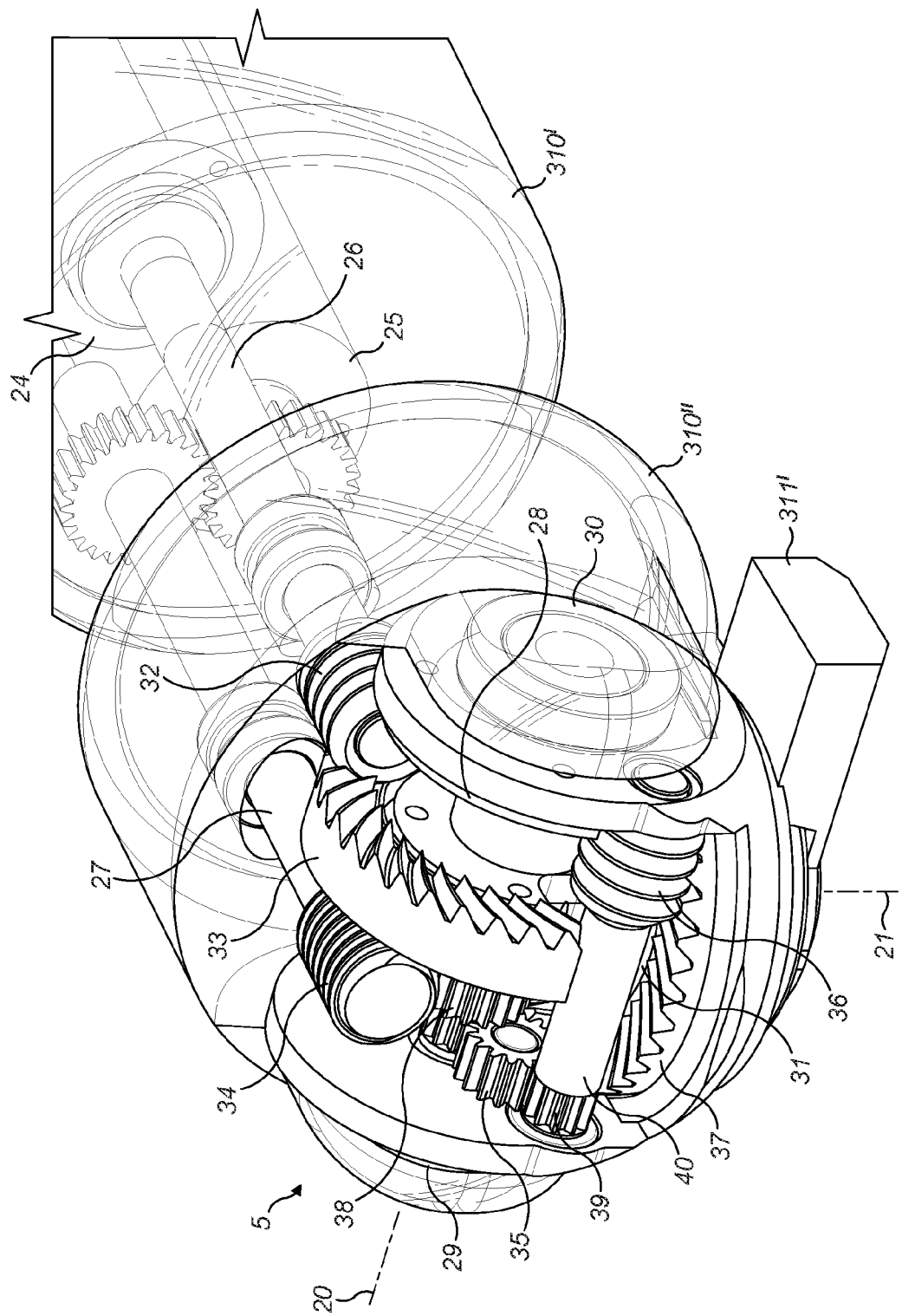
FIG. 4 shows part of the first wrist mechanism from distally and the other side.

FIGS. 3 and 4 show one example of a mechanism suitable for implementing part of the wrist 5 of the arm 1 of FIG. 1. FIGS. 3 and 4 concentrate (as to FIGS. 5 to 10) on the mechanism associated with the joints designated 301 and 302 in FIG. 2.

In the region of the wrist 5 the rigid arm parts 310, 311 have hollow outer shells or casings 310', 310", 311'. The shells define the majority of the exterior surface of the arm, and include a void which is partly or fully encircled by the exterior wall of the respective shell and within which the motors, sensors, cables and other components of the arm can be housed. The shells could be formed of a metal, for example an aluminum alloy or steel, or from a composite, for example a fibre-reinforced resin composite such as resin-reinforced carbon fibre. The shells constitute part of the rigid structure of the arm parts that attaches between the respective joints. The shells may contain a structural framework as shown later in relation to the embodiment of FIG. 7.

In FIGS. 3 and 4, for clarity the shell of arm part 310 is shown in two parts: 310' and 310", both of which are drawn in outline and exploded from each other. The shells of arm parts 4b and 4c are omitted, as is the mechanism associated with joints 300 and 303. The shell of arm part 311 is shown in part, the majority extending from spur 311'.

The shell of arm part 310 (constituted by shell parts 310' and 310") and the shell of arm part 311 (which extends from spur 311') are movable with respect to each other about two rotation axes, shown at 20 and 21. These correspond to axes 305, 306 of FIG. 2. Axes 20 and 21 are orthogonal. Axes 20 and 21 intersect. A central coupler 28 is mounted to arm part 310 by bearings 29, 30. The coupler extends between the bearings 29, 30. The bearings 29, 30 hold the coupler fast with arm part 310 except that they permit relative rotation of the coupler and that arm part about axis 20, thus defining a revolute joint corresponding to joint 301 of FIG. 2. A further bearing 31 attaches the distal shell connector spur 311' to the coupler 28. Bearing 31 holds the distal shell connector spur 311' fast with the coupler 28 except for permitting relative motion of the spur and the coupler about axis 21, thus defining a revolute joint corresponding to joint 302 of FIG. 2.

Two electric motors 24, 25 (see FIG. 4) are mounted in arm part 310. The motors drive respective drive shafts 26, 27 which extend into the midst of the wrist mechanism. Shaft 26 drives rotation about axis 20. Shaft 27 drives rotation about axis 21. Drive shaft 26 terminates at its distal end in a worm gear 32. The worm gear 32 engages a bevel gear 33 which is fast with the coupler 28. Drive shaft 27 terminates at its distal end in a worm gear 34. The worm gear 34 engages a gear train shown generally at 35 which terminates in a further worm gear 36. Worm-form pinion gear 36 engages a hypoid-toothed bevel gear 37 which is fast with the distal shell connector 311'.

Gear 33 is formed as a sector gear: that is its operative arc (defined in the example of FIGS. 3 and 4 by the arc of its teeth) is less than 360°.

The gear train 35 is borne by the coupler 28. The gear train comprises an input gear 38 which engages the worm 34. Input gear 38 is located with its rotation axis relative to the coupler 28 being coincident with axis 20. That means that the input gear can continue to engage the worm 34 irrespective of the configuration of the coupler 28 relative to arm part 310 about axis 20. A series of further gears whose axes are parallel with axis 20 transfer drive from the input gear 38 to an output gear 39 on a shaft 40 whose rotation axis relative to the carrier 28 is parallel with but offset from axis 20. Shaft 40 terminates in the worm 36. Shaft 40 extends parallel to axis 20. The gears of gear train 35, together with shaft 40, are borne by the coupler 28.

The operation of the wrist mechanism will now be described. For motion about axis 20, motor 24 is operated to drive shaft 26 to rotate relative to arm part 310. This drives the bevel gear 33 and hence coupler 28 and distal shell spur 311' to rotate about axis 20 relative to arm part 310. For motion about axis 21, motor 25 is operated to drive shaft 27 to rotate relative to arm part 310. This drives the bevel gear 37 and hence distal shell connector 311' to rotate about axis 21 relative to arm part 310. It will be observed that if drive shaft 26 is rotated, driving the coupler 28 to rotate, whilst drive shaft 27 remains stationary then gear 38 will also rotate relative to the coupler 28, causing parasitic motion of the distal shell connector spur 311' about axis 21. To prevent this, the control system 10 of the arm is configured so that when required there is compensatory motion of drive shaft 27 in tandem with motion of drive shaft 26 so as to isolate motion about axis 21 from motion about axis 20. For example, if it is required to cause relative motion of shells 310, 311 about only axis 20 then motor 24 is operated to cause that motion whilst motor 25 is simultaneously operated in such a way as to prevent input gear 38 from rotating relative to carrier 28.

Various aspects of the mechanism shown in FIGS. 3 and 4 are advantageous in helping to make the mechanism particularly compact.

1. It is convenient for bevel gear 33 to be of part-circular form: i.e. its teeth do not encompass a full circle. For example, gear 33 may encompass less than 270° or less than 180° or less than 90°. This allows at least part of the other bevel gear 37 to be located in such a way that it intersects a circle coincident with gear 33, about the axis of gear 33 and having the same radius as the outermost part of gear 33. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 20 is restricted.
2. It is convenient if the part gear 33 serves rotation about the axis 20 by which the carrier 28 is pivoted to the next-most-proximal arm part 310, as opposed to rotation about axis 21, since the part gear can also be cut away to accommodate shaft 40 intersecting the said circle. That saves space by permitting the worm 36 to be located on the opposite side of bevel gear 33 to the gear train 35. However, in other designs the part gear could serve rotation about axis 21, so gear 37 could be of part-circular form.
3. It is convenient if the worms 32, 34 are located on the opposite side of axis 20 to bevel gear 37: i.e. that there is a plane containing axis 20 on one side of which are the worms 32, 34 and on the other side of which is the bevel gear 37. This helps to provide a compact packaging arrangement.
4. It is convenient if the worm 34 is located on the opposite side of bevel gear 33 from worm 36 and/or that the gear train 35 is located exclusively on the opposite side of bevel gear 33 from worm 36. This again helps to provide a compact packaging arrangement.
5. The gears 33 and/or 37 are conveniently provided as bevel gears since that permits them to be driven from worms located within the plan of their respective external radii. However, they could be externally toothed gears engaged on their outer surfaces by the worms 32, 34 or by radially toothed gears.
6. The bevel gear 33 is conveniently located so as to be interposed between worms 32 and 34. This helps the packaging of the motors 24, 25.
7. The bevel gears and the worm gears that mate with them can conveniently be of hypoid or skew axis, e.g. Spiroid®, form. These gears allow for relatively high torque capacity in a relatively compact form.

Figure 5:
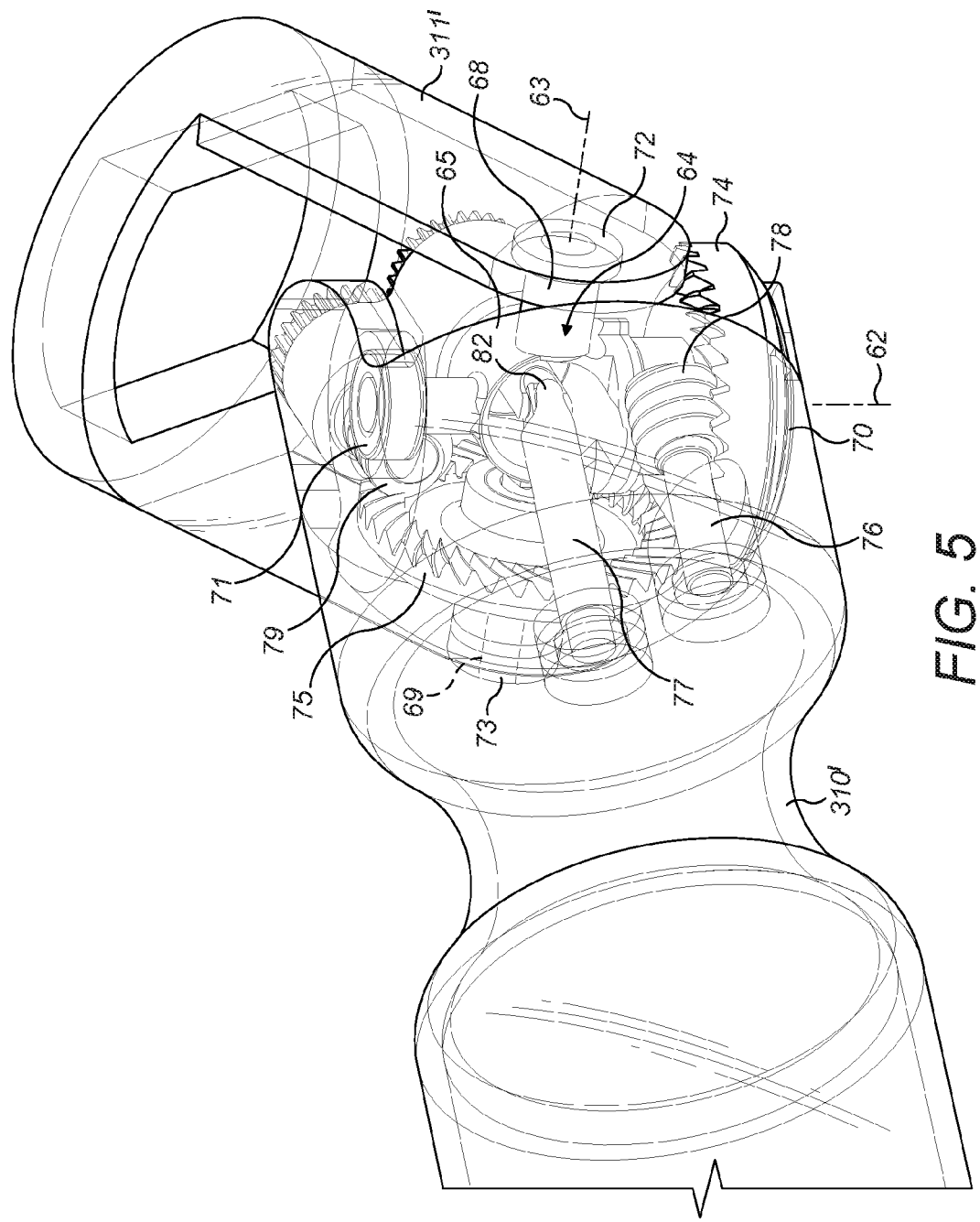
FIG. 5 shows part of a second wrist mechanism from proximally and one side.
Figure 6:
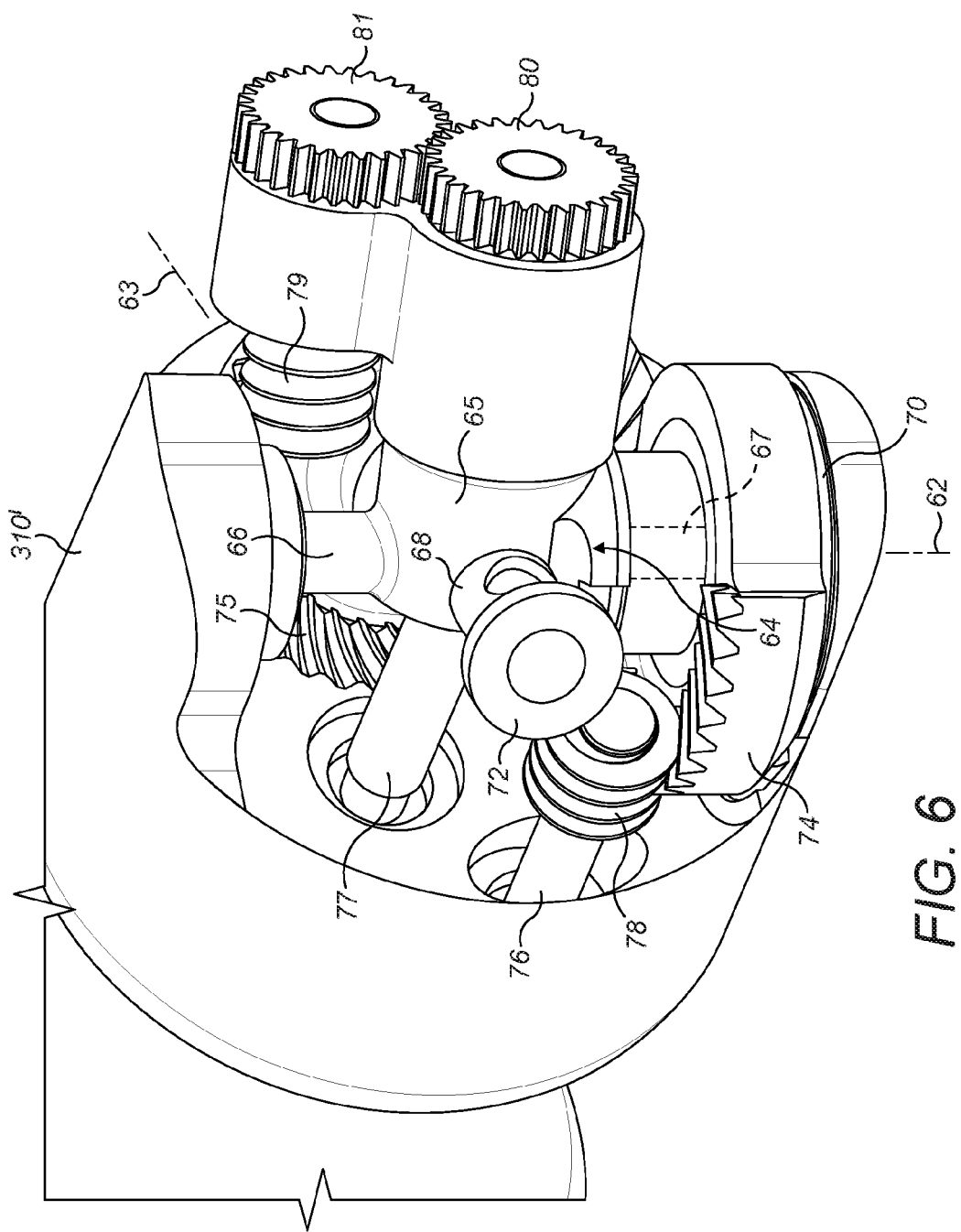
FIG. 6 shows part of the second wrist mechanism from distally and one side.
Figure 7:
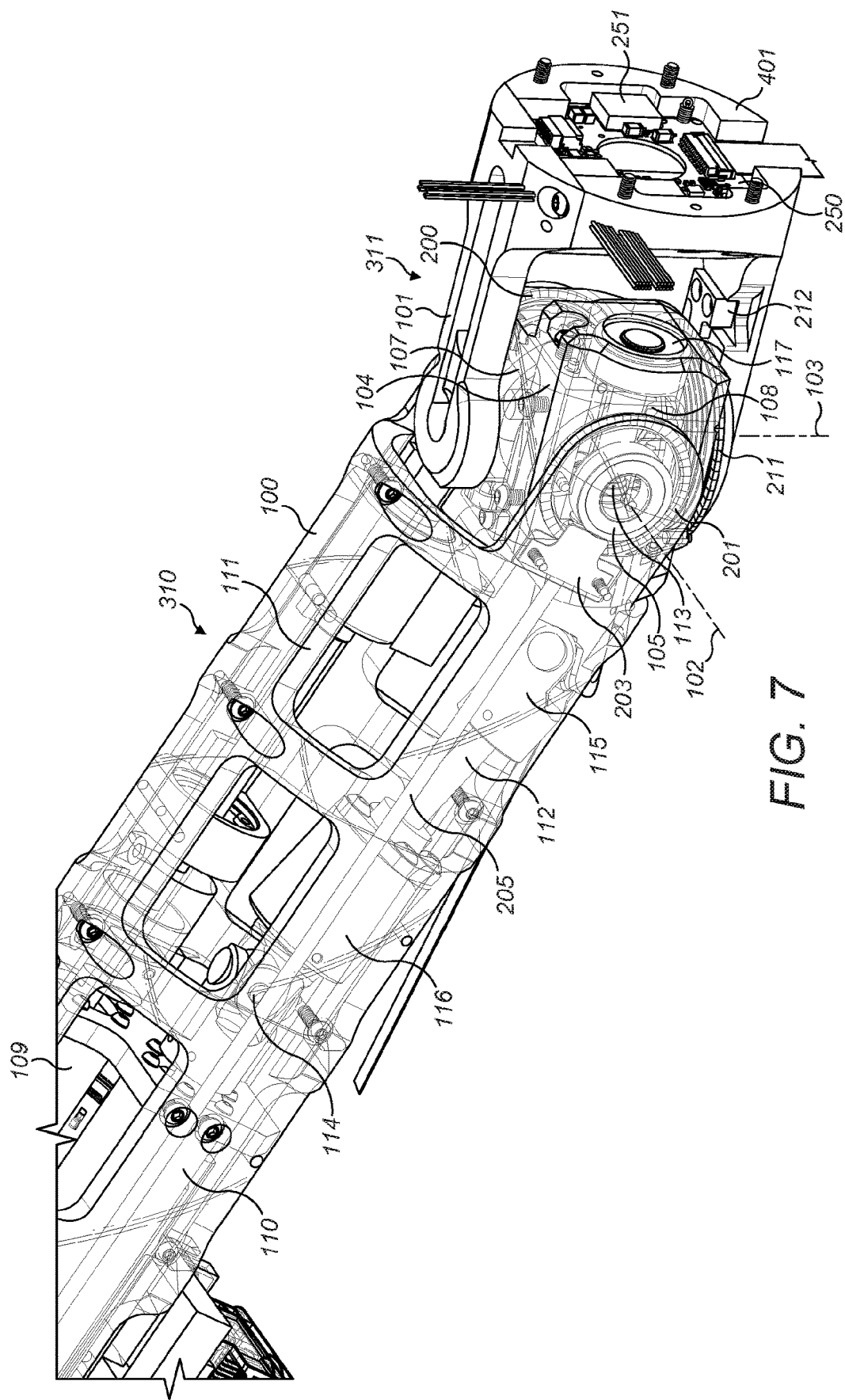
FIG. 7 shows a third wrist mechanism from distally and one side.
Figure 8:
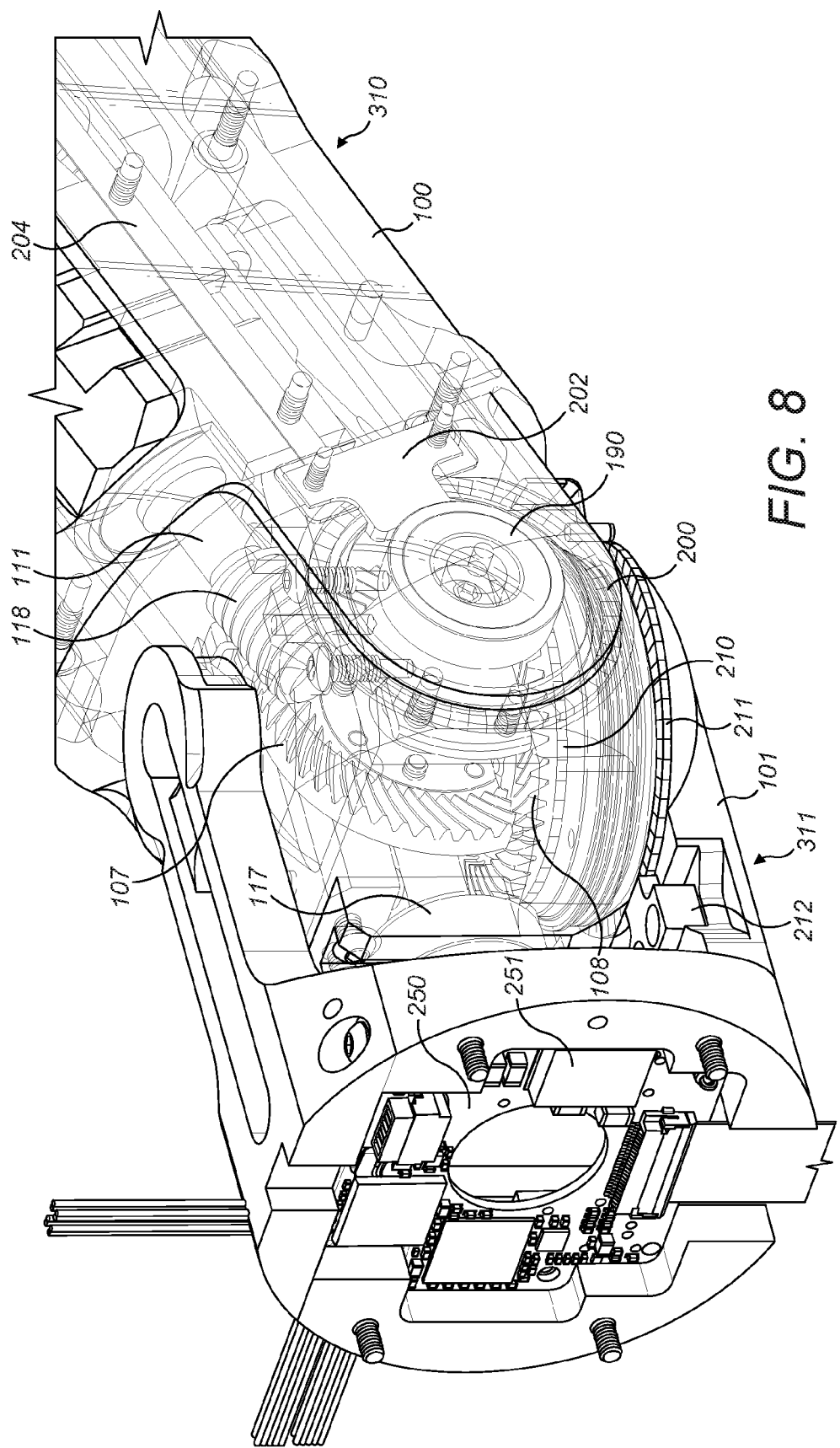
FIG. 8 shows the third wrist mechanism from distally and the other side.

FIGS. 5 and 6 show a second form of wrist mechanism suitable for providing joints 301, 302 in a wrist of the type shown in FIG. 2.

As shown in FIG. 5 the wrist comprises a pair of rigid external shells 310', 311' which define the exterior surfaces of arm parts 310, 311 respectively of FIG. 2. 310' is the more proximal of the shells. The arm parts formed of the shells 310', 311' can pivot relative to each other about axes 62, 63, which correspond respectively to axes 305, 306 of FIG. 2. Axes 62, 63 are orthogonal. Axes 62, 63 intersect. The shells 310', 311' define the exterior of the arm in the region of the wrist and are hollow, to accommodate a rotation mechanism and space for passing cables etc., as will be described in more detail below. The shells could be formed of a metal, for example an aluminium alloy or steel, or from a composite, for example a fibre-reinforced resin composite such as resin-reinforced carbon fibre. The shells constitute the principal rigid structure of the arm parts that attaches between the respective joints.

FIG. 6 shows the same mechanism from distally and one side, with the shell 311' removed for clarity.

Shell 310' is coupled to shell 311' by a cruciform coupler 64. The coupler has a central tube 65 which defines a duct through its centre, running generally along the length of the arm. Extending from the tube are first arms 66, 67 and second arms 68, 69. Each of the shells 310', 311' is attached to the coupler 64 by a revolute joint: i.e. in such a way that it is confined to be able to move relative to the coupler only by rotation about a single axis. The first arms 66, 67 attach to shell 310' by bearings 70, 71 which permit rotation between those first arms and the shell 310' about axis 62. The second arms 68, 69 attach to shell 311' by bearings 72, 73 which permit rotation between those second arms and the shell 311' about axis 63. A first bevel gear 74 is concentric with the first arms 66, 67. The first bevel gear is fast with the coupler 64 and rotationally free with respect to the proximal one of the two shells 310'. A second bevel gear 75 is concentric with the second arms 68, 69. The second bevel gear is fast with the distal one of the two shells 311' and rotationally free with respect to the coupler 64.

Two shafts 76, 77 operate the motion of the compound joint. The shafts extend into the central region of the joint from within the proximal one of the shells 310'. Each shaft is attached at its proximal end to the shaft of a respective electric motor (not shown), the housings of the motors being fixed to the interior of the proximal shell 310'.

In this way the shafts 76, 77 can be driven by the motors to rotate with respect to the proximal shell 310'.

Shaft 76 and its associated motor operate motion about axis 62. Shaft 76 terminates at its distal end in a worm gear 78 which engages bevel gear 74. Rotation of shaft 76 causes rotation of the bevel gear 74 relative to shell 31O' about axis 62. Bevel gear 74 is fast with the coupler 64, which in turn carries the distal shell 311'. Thus rotation of shaft 76 causes relative rotation of the shells 31O', 311' about axis 62.

Shaft 77 and its associated motor operate motion about axis 63. In order to do that it has ultimately to drive bevel gear 75 by means of a worm gear 79 carried by the coupler 64. Rotation of that worm gear can cause relative rotation of the coupler and the distal shell 311'. To achieve this, drive is transmitted from the shaft 77 through a pair of gears 80, 81 borne by the carrier 64 to a shaft bearing the worm gear 79. Shaft 77 approaches the carrier 64 from the proximal side. The gears 80, 81 are located on the distal side of the coupler. The shaft 77 passes through the duct defined by tube 65 in the centre of the coupler. To accommodate motion of the coupler 64 relative to the first shell 31O' the shaft 77 has a universal or Hooke's joint 82 along its length. The universal joint 82 lies on axis 62. Instead of a Hooke's joint the shaft could have another form of flexible coupling, for example an elastic coupling (which could be integral with the shaft) or a form of constant velocity joint.

This mechanism has been found to be capable of providing a particularly compact, light and rigid drive arrangement for rotation about axes 62 and 63 without the components of the mechanism unduly restricting motion of the shells. It permits both motors to be housed in the proximal shell which reduces distal weight.

Various aspects of the mechanism shown in FIGS. 5 and 6 are advantageous in helping to make the mechanism particularly compact.

1. It is convenient for bevel gear 74 to be of part-circular form: i.e. its teeth do not encompass a full circle. For example, gear 74 may encompass less than 270° or less than 180° or less than 90°. This allows at least part of the other bevel gear 75 to be located in such a way that it intersects a circle coincident with gear 74, about the axis of gear 74 and having the same radius as the outermost part of gear 74. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 62 is restricted. As shown in FIG. 6, the bevel gear 74 is of reduced radius in the region not encompassed by its teeth. Part-circular bevel gears of the other embodiments may be formed in the same manner.
2. The gears 74 and/or 75 are conveniently provided as bevel gears since that permits them to be driven from worms located within the plan of their respective external radii. However, they could be externally toothed gears engaged on their outer surfaces by the worms 76, 79, or by radially toothed gears.
4. The bevel gears and the worm gears that mate with them can conveniently be of skew axis, e.g. Spiroid®, form. These allow for relatively high torque capacity in a relatively compact form.

FIGS. 7 to 10 illustrate another form of wrist mechanism. In these figures the shells of arm parts 310, 311 are omitted, exposing the structure within the arm parts. Proximal arm part 310 has a structural framework 100, which is shown in outline in some of the figures. Distal arm part 311 has a structural framework 101. Arm parts 310 and 311 are rotatable relative to each other about axes 102, 103, which correspond to axes 305, 306 respectively of FIG. 2. A carrier 104 couples the arm parts 310, 311 together. Carrier 104 is attached by bearings 105, 190 to arm part 310. Those bearings define a revolute joint about axis 102 between arm part 310 and the carrier 104. Carrier 104 is attached by bearing 106 to arm part 311. Those bearings define a revolute joint about axis 103 between arm part 311 and the carrier 104. A first bevel gear 107 about axis 102 is fast with the carrier 104. A second bevel gear 108 about axis 103 is fast with arm part 311.

As with the other mechanisms described herein, the carrier 104 is located inboard of the limbs 310, 311.

Two motors 109, 110 are fixed to the framework 100 of arm part 310. Motor 109 drives a shaft 111. Shaft 111 is rigid and terminates in a worm 118 which engages bevel gear 107. When motor 109 is operated, shaft 111 rotates relative to the proximal arm part 310, driving bevel gear 107 and hence coupler 104 and arm part 311 to rotate relative to arm part 310 about axis 102. Motor 110 drives a shaft 112. Shaft 112 has a worm 113 near its distal end which engages bevel gear 108. To accommodate motion of bevel gear 108 relative to motor 110 when the coupler 104 moves about axis 102 shaft 112 includes a pair of universal joints 114, 115 and a splined coupler 116 which accommodates axial extension and retraction of shaft 112. The final part of shaft 112 is mounted to the coupler 104 by bearing 117.

It is convenient for bevel gear 107 to be of part-circular form: i.e. its teeth do not encompass a full circle. For example, gear 107 may encompass less than 270° or less than 180° or less than 90°. This allows at least part of the other bevel gear 108 to be located in such a way that it intersects a circle coincident with gear 107, about the axis of gear 107 and having the same radius as the outermost part of gear 107. Whilst this feature can be of assistance in reducing the size of a range of compound joints, it is of particular significance in a wrist of the type shown in FIG. 2, comprising a pair of roll joints with a pair of pitch/yaw joints between them, since in a joint of that type there is a degree of redundancy among the pitch/yaw joints and hence a wide range of positions of the distal end of the arm can be reached even if motion about axis 102 is restricted.

The gears 107 and/or 108 are conveniently provided as bevel gears since that permits them to be driven from worms located within the plan of their respective external radii. However, they could be externally toothed gears engaged on their outer surfaces by the worms attached to shafts 111, 112, or by externally toothed gears.

The bevel gears and the worm gears that mate with them can conveniently be of skew axis, e.g. Spiroid®, form. These allow for relatively high torque capacity in a relatively compact form.

Various changes can be made to the mechanisms described above. For example, and without limitation:
 The axes corresponding to axes 305, 306 need not intersect and need not be orthogonal.
 The bevel gears or their outer toothed gear equivalents need not be driven by worms. They could be driven by other gears.
 Either or both bevel gears could be part gears.
 In the examples given above, the mechanisms form part of a wrist for a robot arm. The mechanisms could be used for other applications, for example for other parts of robot arms, for robot tools, and for non-robotic applications such as control heads for cameras.

As discussed above with reference to FIG. 1, each joint is provided with a torque sensor which senses the torque applied about the axis of that joint. Data from the torque sensors is provided to the control unit 10 for use in controlling the operation of the arm.

Figure 9:
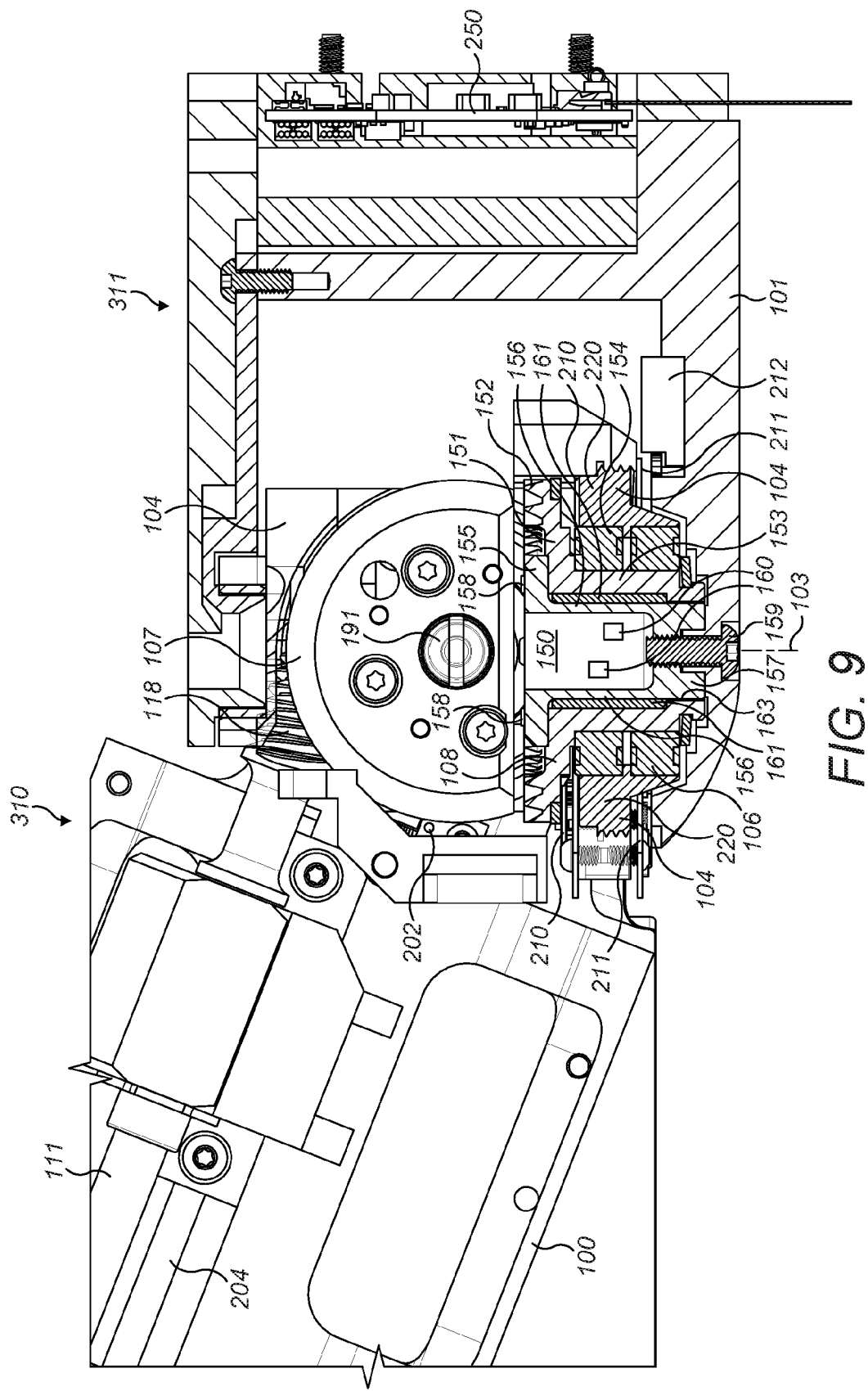
FIG. 9 shows the third wrist mechanism in section on a central longitudinal plane viewed from one side.
Figure 10:
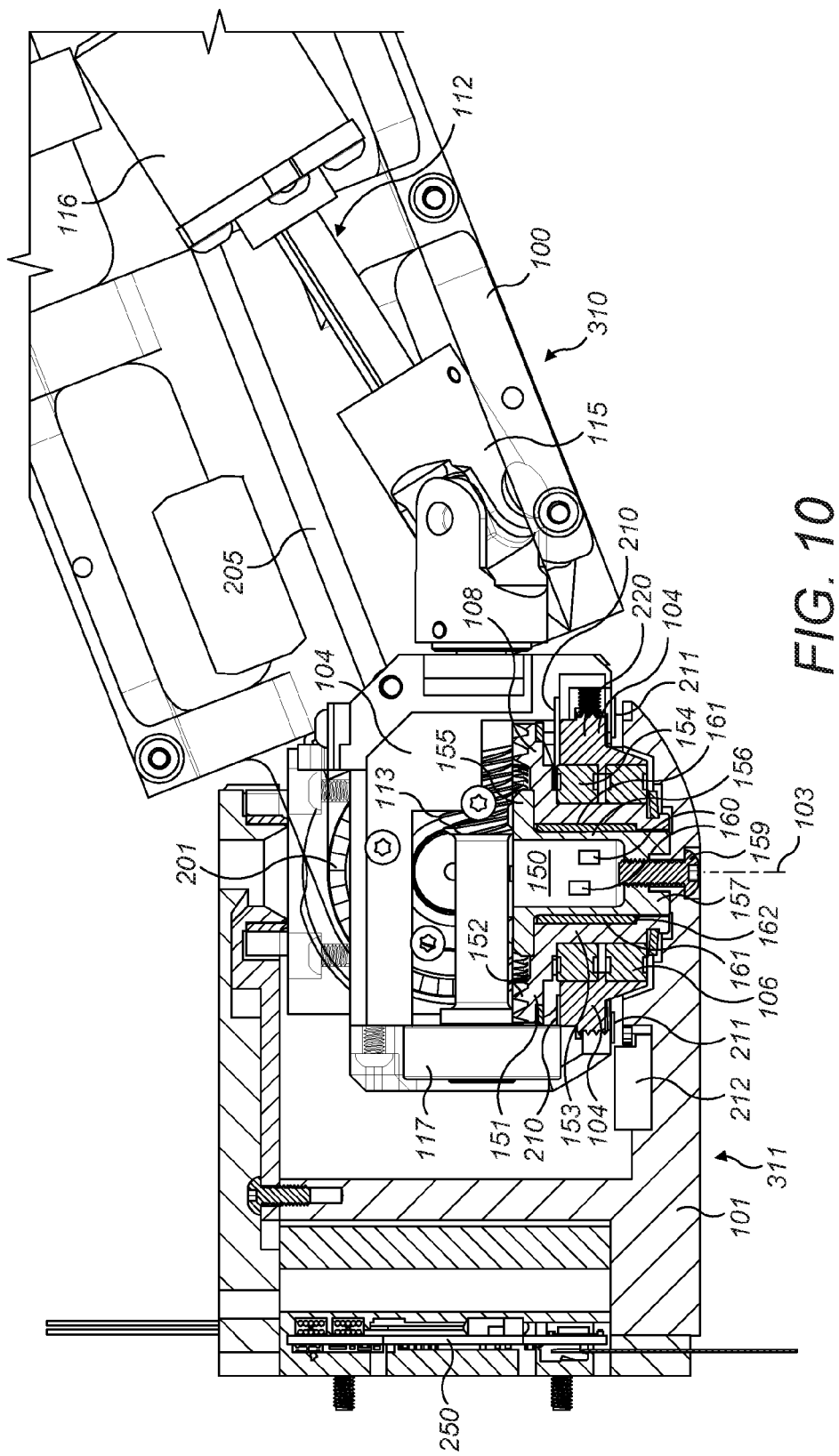
FIG. 10 shows the third wrist mechanism in section on a central longitudinal plane viewed from the other side.

FIGS. 9 and 10 shows one of the torque sensors and its mounting arrangement in cross-section. Torque sensor 150 measures the torque applied about axis 103: that is from carrier 104 to distal arm frame 101. As described above, bevel gear 108 is fast with frame 101 and rotatable about axis 103 with respect to the carrier 104. Bevel gear 108 comprises a radially extending gear portion 151, from which its gear teeth 152 extend in an axial direction, and an axially extending neck 153. The neck, the radially extending gear portion and the teeth are integral with each other. The interior and exterior walls of the neck 153 are of circularly cylindrical profile. A pair of roller or ball bearing races 106, 154 fit snugly around the exterior of the neck. The bearings sit in cups in the carrier 104 and hold the neck 153 in position relative to the carrier whilst permitting rotation of the bevel gear 108 relative to the carrier about axis 103.

The torque sensor 150 has a radially extending top flange 155, an axially elongate torsion tube 156 which extends from the top flange, and an internally threaded base 157 at the end of the torsion tube opposite the flange. The top flange 155 abuts the gear portion 151 of the bevel gear 108. The top flange is held fast with the gear portion by bolts 158. The torsion tube 156 extends inside the neck 153 of the bevel gear 108. The exterior wall of the torsion tube is of circularly cylindrical profile. The exterior of the base 157 is configured with a splined structure which makes positive engagement with a corresponding structure in the frame 101 so as to hold the two in fixed relationship about axis 103. A bolt 159 extends through the frame 101 and into the base 157 to clamp them together. Thus, it is the torque sensor 150 that attaches the bevel gear 108 to the arm frame 101, and the torque applied about axis 103 is applied through the torque sensor. The torsion tube has a hollow interior and a relatively thin wall to its torsion tube 150. When torque is applied through the torque sensor there is slight torsional distortion of the torsion tube. The deflection of the torsion tube is measured by strain gauges 160 fixed to the interior wall of the torsion tube. The strain gauges form an electrical output indicative of the torsion, which provides a representation of the torque about axis 103. The strain gauges could be of another form: for example optical interference strain gauges which provide an optical output.

In order to get the most accurate output from the torque sensor, torque transfer from the bevel gear 108 to the frame 101 in a way that bypasses the torsion tube 156 should be avoided. For that reason, it is preferred to reduce friction between the neck 153 of the bevel gear 108 and the base 157 of the torque sensor. One possibility is to provide a gap between the neck of the bevel gear and both the base of the torque sensor and the torsion tube. However, that could permit shear forces to be applied to the torsion tube in a direction transverse to axis 103, which would itself reduce the accuracy of the torque sensor by exposing the strain gauges 160 to other than torsional forces. Another option is to introduce a bearing race between the interior of the neck of bevel gear 108 and the exterior of the base 157 of the torque sensor. However, that would substantially increase the volume occupied by the mechanism. Instead, the arrangement shown in FIG. 8 has been shown to give good results. A sleeve or bushing 161 is provided around the torsion tube 156 and within the neck 153 of the bevel gear 108. The sleeve is sized so that it makes continuous contact with the interior wall of the neck 153 and with the exterior wall of the torsion tube 156, which is also of circularly cylindrical profile. The whole of the interior surface of the sleeve makes contact with the exterior of the torsion tube 156. The whole of the exterior surface of the sleeve makes contact with the interior surface of the neck 153. The sleeve is constructed so that it applies relatively little friction between the neck and the torsion tube: for instance the sleeve may be formed of or coated with a low-friction or self-lubricating material. The sleeve is formed of a substantially incompressible material so that it can prevent deformation of the torque sensor under shear forces transverse to the axis 103. For example, the sleeve may be formed of or coated with a plastics material such as nylon, polytetrafluoroethylene (PTFE), polyethylene (PE) or acetal (e.g. Delrin®), or of graphite or a metal impregnated with lubricant.

For easy assembly of the mechanism, and to hold the sleeve 161 in place, the interior wall of the neck 153 of the bevel gear 108 is stepped inwards at 162, near its end remote from the radially extending gear portion 151. When the sleeve 161 is located between the neck 153 and the torsion tube 156, and the head 155 of the torque sensor is bolted to the gear portion 151 the sleeve is held captive both radially (between the torsion tube and the neck) and axially (between the head 155 of the torque sensor and the step 162 of the interior surface of the neck 153 of the bevel gear). It is preferred that the internal radius of the neck 153 in the region 163 beyond the step 162 is such that the internal surface of the neck in that region is spaced from the torque sensor 150, preventing frictional torque transfer between the two.

Similar arrangements can be used for the torque sensor about the other axis 102 of the embodiment of FIGS. 7 to 10, and for the torque sensors of the embodiments of the other figures.

Hall effect sensors are used to sense the rotational position of the joints. Each position sensor comprises a ring of material arranged around one of the rotation axes. The ring has a series of regularly spaced alternating north and south magnetic poles. Adjacent to the ring is a sensor chip with a sensor array comprising multiple Hall effect devices which can detect the magnetic field and measure the position of the magnetic poles on the ring relative to the sensor array so as to provide a multi-bit output indicative of that relative position. The rings of magnetic poles are arranged such that each position of the respective joint within a 360° range is associated with a unique set of outputs from the pair of magnetic sensors. This may be achieved by providing different numbers of poles on each ring and making the numbers of poles the rings co-prime to each other. Hall effect position sensors employing this general principle are known for use in robotics and for other applications.

More specifically, associated with each joint is a pair of alternatingly magnetised rings, and associated sensors. Each ring is arranged concentrically about the axis of its respective joint. The rings are fast with an element on one side of the joint and the sensors are fast with an element on the other side of the joint, with the result that there is relative rotational motion of each ring and its respective sensor when there is rotation of the robot arm about the respective joint. Each individual sensor measures where between a pair of poles the associated ring is positioned relative to the sensor. It cannot be determined from the output of an individual sensor which of the pole pairs on the ring is above the sensor. Thus the individual sensors can only be used in a relative fashion and would require calibration at power up to know the absolute position of the joint. However by using a pair of rings designed so that the numbers of pole pairs in each ring has no common factors it is possible to combine the inter-pole pair measurement from both sensors and work out the absolute position of the joint without calibration.

The magnetic rings and sensors are shown in FIGS. 7 to 10. For the joint that provides rotation about axis 102 position is sensed by means of magnetic rings 200 and 201 and sensors 202 and 203. For the joint that provides rotation about axis 103 position is sensed by means of magnetic rings 210, 211, sensor 212 and a further sensor that is not shown. Magnetic ring 200 is fast with carrier 104 and mounted on one side of the carrier. Magnetic ring 201 is fast with carrier 104 and mounted on the other side of the carrier to magnetic ring 200. The magnetic rings 200, 201 are planar, and arranged perpendicular to and centred on axis 102. Sensors 202 and 203 are fast with the frame 100 of the arm part 310. Sensor 202 is mounted so as to be adjacent to a side of ring 200. Sensor 203 is mounted so as to be adjacent to a side of ring 201. Cables 204, 205 carry the signals from the sensors 202, 203. Magnetic ring 210 is fast with carrier 104 and mounted on one side of a flange 220 of the carrier. Magnetic ring 211 is fast with carrier 104 and mounted on the other side of the flange 220 to magnetic ring 200. The magnetic rings 210, 211 are planar, and arranged perpendicular to and centred on axis 103. Sensor 212 and the other sensor for rotation about axis 103 are fast with the frame 101 of the arm part 311. Sensor 212 is mounted so as to be adjacent to a side of ring 210. The other sensor is mounted so as to be adjacent to a side of ring 211.

Thus, in the arrangement of FIGS. 7 to 10, rotation about each of the axes 102, 103 is sensed by means of two multipole magnetic rings, each with a respective associated sensor. Each sensor generates a multi-bit signal representing the relative position of the nearest poles on the respective ring to the sensor. By arranging for the numbers of poles on the two rings to be co-prime the outputs of the sensors are in combination indicative of the configuration of the joint within a 360° range. This permits the rotation position of the joint to be detected within that range. Furthermore, in the arrangement of FIGS. 7 to 10 the two rings associated with each joint (i.e. rings 200, 201 on the one hand and rings 210, 211 on the other hand) are located so as to be substantially offset from each other along the axis of the respective joint. Ring 200 is located near the bearing 190 on one side of the body of carrier 104 whereas ring 201 is located near bearing 105 on the opposite side of the carrier 104. Ring 210 is located on one side of the flange 220 whereas ring 211 is located on the other side of the flange 220. Each ring is made of a sheet of material which is flat in a plane perpendicular to the axis about which the ring is disposed. The magnetic rings of each pair (i.e. rings 200, 201 on the one hand and rings 210, 211 on the other hand) are spaced from each other in the direction along their respective axes by a distance greater than 5 and more preferably greater than 10 or greater than 20 times the thickness of the rings of the pair. Conveniently, the rings of a pair can be on opposite sides of the respective joint, as with rings 200, 201. Conveniently the carrier 104 to which the both rings of a pair are attached extends radially outwardly so as to lie at a radial location that is between the rings when viewed in a plane containing the respective rotation axis. Thus, for example, flange 220 lies radially between rings 210 and 211. Conveniently the respective joint can be supported or defined by two bearings, one on either side of the joint along the respective axis, and at extreme locations on the joint, and the or each ring for that joint can overlap a respective one of the bearings in a plane perpendicular to the axis. Conveniently the sensors for the rings can be mounted on an arm part that is articulated by the joint. The sensors can be mounted on opposite sides of the arm part.

By spacing the rings apart the packaging of the joint and/or of the arm part where the associated sensors are mounted can be greatly improved. Spacing the rings apart allows for more opportunities to locate the rings at a convenient location, and allows the sensors to be spaced apart, which can itself provide packaging advantages. It is preferred that the joint is sufficiently stiff in comparison to the number of magnetic poles on the rings that torsion of the joint under load will not adversely affect measurement. For example it is preferred that the joint is sufficiently stiff that under its maximum rated operating load the elements of the joint cannot twist so much that it can cause a change in the order of magnetic transitions at the sensors, even though they are spaced apart. That permits direction to be detected, in addition to motion, for all load conditions.

Arm part 311 is distal of arm part 310. Arm part 310 is proximal of the joint about axes 102 and 103 shown in FIG. 7 to 10. As discussed with reference to FIG. 1, data from the torque sensors and the position sensors to be fed back to the control unit 10. It is desirable for that data to be passed by wired connections that run through the arm itself.

Each arm part comprises a circuit board. FIGS. 7 to 10 show a circuit board 250 carried by arm part 311. Each circuit board includes a data encoder/decoder (e.g. integrated circuit 251). The encoder/decoder converts signals between formats used locally to the respective arm part and a format used for data transmission along the arm. For example: (a) locally to the arm part the position sensors may return position readings as they are passed by magnetic pole transitions, the torque sensor may return an analogue or digital signal indicative of the currently sensed torque and the drive motors may require a pulse width modulated drive signal; whereas (b) for data transmission along the arm a generic data transmission protocol, which may be a packet data protocol such as Ethernet, can be used. Thus the encoders/decoders can receive data packets conveyed along the arm from the control unit 10 and interpret their data to form control signals for any local motor, and can receive locally sensed data and convert it into packetized form for transmission to the control unit. The circuit boards along the arm can be chained together by communication cables, so that communications from a relatively distal board go via the more proximal boards.

In general it is desirable not to feed data from one component of the arm to a more distal component of the arm. Doing so would involve cables running unnecessarily distally in the arm, increasing distally distributed weight; and since the circuit boards are chained together once data has been sent to a relatively distal board the next most proximal board will handle the data anyway in order to forward it.

The compound joint about axes 102, 103 has rotary position sensors 202, 203 (for rotation about axis 102) and 212 (for rotation about axis 103). Sensors 202, 203 are mounted on the frame 100 of the arm part 310 that is proximal of the joint whose motion is measured by the sensor. Data from position sensors 202, 203 is fed along cables 204, 205 which lead along arm part 310 proximally of the sensors. Sensor 202 is mounted on the frame 101 of the arm part 311. Data from position sensor 202 is fed along a cable to circuit board 250 on the same arm part. In each case the data is not passed to a more distal element of the arm than the one where the data was collected.

The compound joint about axes 102, 103 has torque sensors 150 (for rotation about axis 103) and 191 (for rotation about axis 102). Data sensed by torque sensors 150, 191 is carried in native form to circuit board 250 by flexible cables. At circuit board 250 the encoder/decoder 251 encodes the sensed data, e.g. to Ethernet packets, and transmits it to the control unit 10. Thus, rather than being fed to the circuit board of the more proximal arm part 310 for encoding, the data from the torque sensors is passed to the circuit board of the more distal arm part for encoding, and then from that circuit board it is passed by cables in a distal direction along the arm.

Figure 11:
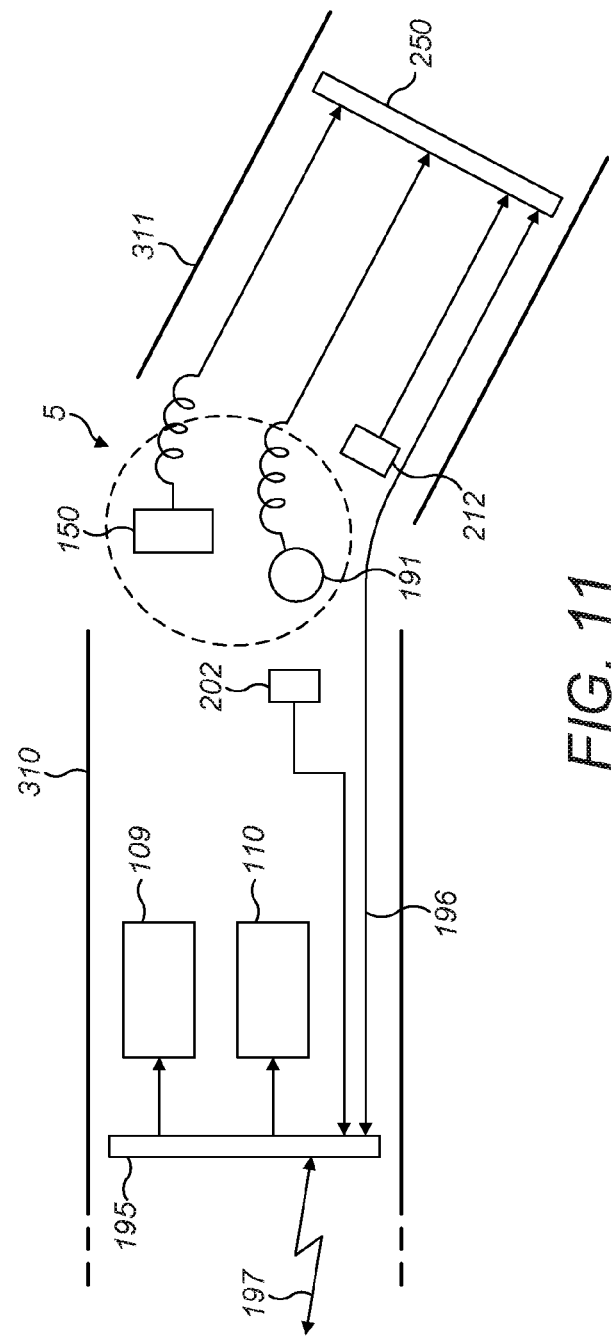
FIG. 11 illustrates communication paths in a robot arm.

This arrangement is illustrated in FIG. 11. Arm part 310 comprises circuit board 195 which receives data from position sensor 202 and provides command data to motors 109, 110. Arm part 311 comprises circuit board 250 which receives data from position sensor 212 and torque sensors 150, 191. Circuit board 250 encodes that sensed data and passes it over a data bus 196 to circuit board 195, which forwards it on towards control unit 10 via a link 197. Position sensor 202 is connected directly by a cable to circuit board 195. Position sensor 212 and torque sensors 150, 191 are connected directly by cables to circuit board 195.

Figure 12:
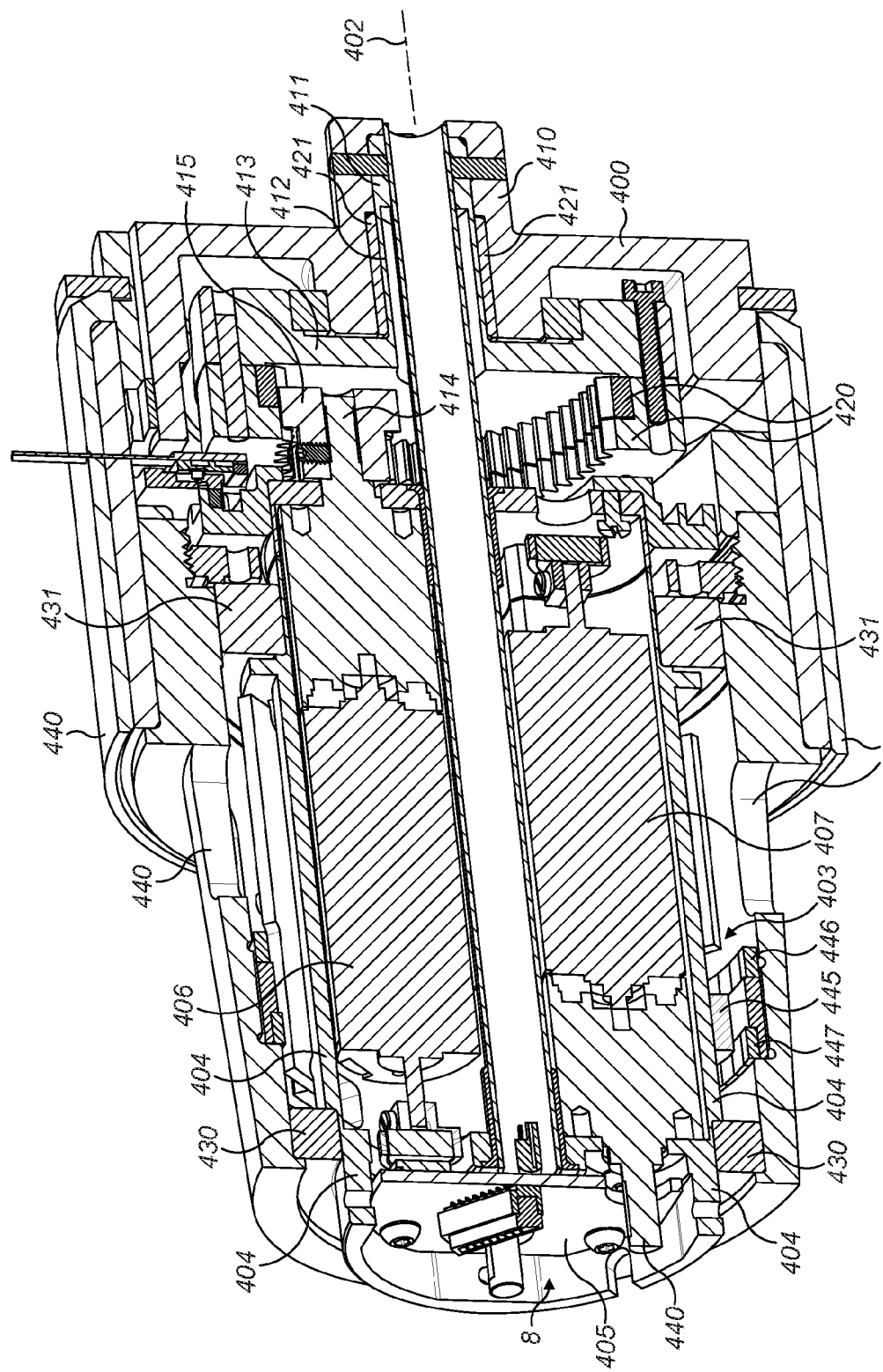
FIG. 12 shows a terminal module for a robot arm in longitudinal cross-section.

As illustrated in FIG. 2, arm part 4c is borne by arm part 311 and can be rotated relative to arm part 4c about axis 307. FIG. 12 shows a cross-section through a module that comprises arm part 4c. The module has a base 400 and a side-wall 440 which is fast with the base. Base 400 attaches to the end face 401 of the distal end of arm part 311. (See FIG. 7). Arm part 4c is indicated generally at 403. Arm part 4c is rotatable relative to the base about an axis 402 corresponding to axis 307 of FIG. 2. To that end, arm part 4c is mounted to the side-wall 440 by bearings 430, 431 which define a revolute joint between side wall 440 and arm part 4c about axis 402.

Arm part 4c has a housing 404 which houses its internal components. Those components include a circuit board 405 and motors 406, 407. Motors 406, 407 are fixed to the housing 404 so they cannot rotate relative to it. The housing 404 is free to rotate relative to the base 400 by means of the bearings 430, 431. A channel 408 runs through the interior of the module to accommodate a communication cable (not shown) passing from circuit board 250 to circuit board 405. The communication cable carries signals which, when decoded by an encoder/decoder of circuit board 405, cause it to issue control signals to control the operation of motors 406, 407.

Motor 406 drives rotation of arm part 4c relative to arm part 311. Thus, motor 406 drives rotation of housing 404 relative to base 400. Base 400 has a central boss 410. A torque sensor generally of the type discussed in relation to FIGS. 9 and 10 is attached to the boss 410. The torque sensor has an integral member comprising a base 411, a torsion tube 412 and a radially extending head 413. The base 411 of the torque sensor is fast with the boss 410 of the base 400. As with the torque sensor of FIGS. 9 and 10, a sleeve 421 extends around the torsion tube of the torque sensor to protect it from shear forces and to reduce friction between it and the surrounding component, which is the base 400.

An internally toothed gear 420 is fast with the head 413 of the torque sensor. Motor 406 drives a shaft 414 which carries a pinion gear 415. Pinion gear 415 engages the internal gear 420. Thus, when the motor 406 is operated it drives the pinion gear 415 to rotate and this causes the arm part 4c, of which the motor 406 is part, to rotate about axis 402. The resulting torque about axis 402 is transmitted to the base 400 through the torsion tube 412 of the torque sensor, allowing that torque to be measured by strain gauges attached to the torsion tube.

The interface 8 for attachment to an instrument is shown in FIG. 12. The shaft 440 of motor 407 is exposed at the interface for providing drive to an instrument.

Torque data from the torque sensor 411, 412, 413 is passed to circuit board 250 on arm part 311 for encoding. The rotational position of arm part 4c can be sensed by a sensor 445 carried by arm part 4c and which detects transitions between magnetic poles on rings 446, 447 mounted on the interior of housing 404. Data from sensor 445 is passed to circuit board 405 of arm part 4c for encoding.

The motors that drive rotation about joints 102 and 103 are mounted proximally of those joints, in arm part 310. As discussed above, this improves weight distribution by avoiding weight being placed nearer the distal end of the arm. In contrast, the motor that drives rotation of arm part 4c is mounted in arm part 4c rather than in arm part 311. Although this might be seen as disadvantageous due to it requiring motor 406 to be mounted more distally, it has been found that this allows for arm part 311 to be especially compact. Motor 406 can be packaged in arm part 4c in parallel with the motor(s) (e.g. 407) which provide drive to the instrument: i.e. so that the motors intersect a common plane perpendicular to the axis 402. That means that incorporation of motor 406 in arm part 4c need not make arm part 4c substantially longer.

Instead of toothed gears, the drive of the joints could be by frictional means.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A torque sensor arrangement configured to attach between a first part and a second part to sense torque therebetween, the torque sensor arrangement comprising:
    an interface member having on its exterior an engagement configuration configured to rotationally engage the first part;
    a torsion member comprising a deflectable body attached at one end thereof to the interface member and comprising, at the other end of the deflectable body, an engagement configuration configured to fixedly engage the second part; and
    a deflection sensor attached to the deflectable body;
    wherein the interface member defines a rigid sleeve extending around the deflectable body and the torque sensor arrangement further comprises a bushing located between and in contact with both the sleeve and the deflectable body.

2. A torque sensor arrangement as claimed in claim 1, wherein the bushing is a solid bushing.

3. A torque sensor arrangement as claimed in claim 2, wherein the bushing is a unitary tube of material.

4. A torque sensor arrangement as claimed in claim 1, wherein the bushing is formed of plastics material.

5. A torque sensor arrangement as claimed in claim 1, wherein the first part and the second part are configured to mutually rotate about a rotation axis and the bushing surrounds the deflectable body about that axis.

6. A torque sensor arrangement as claimed in claim 1, wherein the bushing is a rigid bushing.

7. A torque sensor as claimed in claim 1, wherein the interface member comprises a shoulder on the opposite end of the sleeve from that at which the torsion member is attached to the interface member, and the torsion member is configured to hold the bushing captive against the shoulder when the torsion member is attached to the interface member.

8. A torque sensor as claimed in claim 1, wherein the deflectable body is a hollow body.

9. A torque sensor as claimed in claim 8, wherein the deflectable body is a hollow cylinder.

10. A torque sensor as claimed in claim 1, wherein the deflection sensor is a strain gauge.

11. A torque sensor as claimed in claim 1, wherein the engagement configuration configured to rotationally engage the first part is a set of gear teeth.

12. A torque sensor as claimed in claim 1, wherein the engagement configuration configured to fixedly engage the second part is a spline coupling.

13. A torque sensor as claimed in claim 1, wherein the interface member is rotationally engaged with the first part and the torsion member is fixedly engaged with the second part.

14. A robot arm comprising two limbs and a torque sensor as claimed in claim 1 configured to sense torque between two limbs of the arm.

* * * * *